United States Patent [19]

Hoberg et al.

[11] Patent Number: 5,175,381
[45] Date of Patent: Dec. 29, 1992

[54] PROCESS FOR RECOVERING HALOGENATED HYDROCARBONS FROM SYNTHETIC FOAMS

[75] Inventors: Heinz Hoberg, Aachen Laurensberg; Joachim Christiani, Saarbruecken; Martin Bender, Aachen, all of Fed. Rep. of Germany

[73] Assignee: SMG Sommer Metallwerke GmbH, Emmering, Fed. Rep. of Germany

[21] Appl. No.: 736,832

[22] Filed: Jul. 29, 1991

[30] Foreign Application Priority Data

Jan. 14, 1991 [DE] Fed. Rep. of Germany ....... 4100875

[51] Int. Cl.5 .............................................. C07C 17/38
[52] U.S. Cl. ..................... 570/177; 570/211; 570/238; 570/262
[58] Field of Search ................ 570/177, 211, 238, 262

[56] References Cited

FOREIGN PATENT DOCUMENTS 0056410 3/1984 Japan .................................. 570/238

Primary Examiner—Marianne M. Cintins
Assistant Examiner—John D. Peabody, III
Attorney, Agent, or Firm—Jordan and Hamburg

[57] ABSTRACT

A method for recovering halogenated hydrocarbons (FCH) from synthetic foams wherein halogenated hydrocarbons (FCH) are released from synthetic foam in a hermetically sealed processing chamber and transferred to a gaseous carrier medium of steam. The steam/FCH mixture is removed from the processing chamber and subjected to condensation to remove pure FCH from the condensed water.

7 Claims, 1 Drawing Sheet

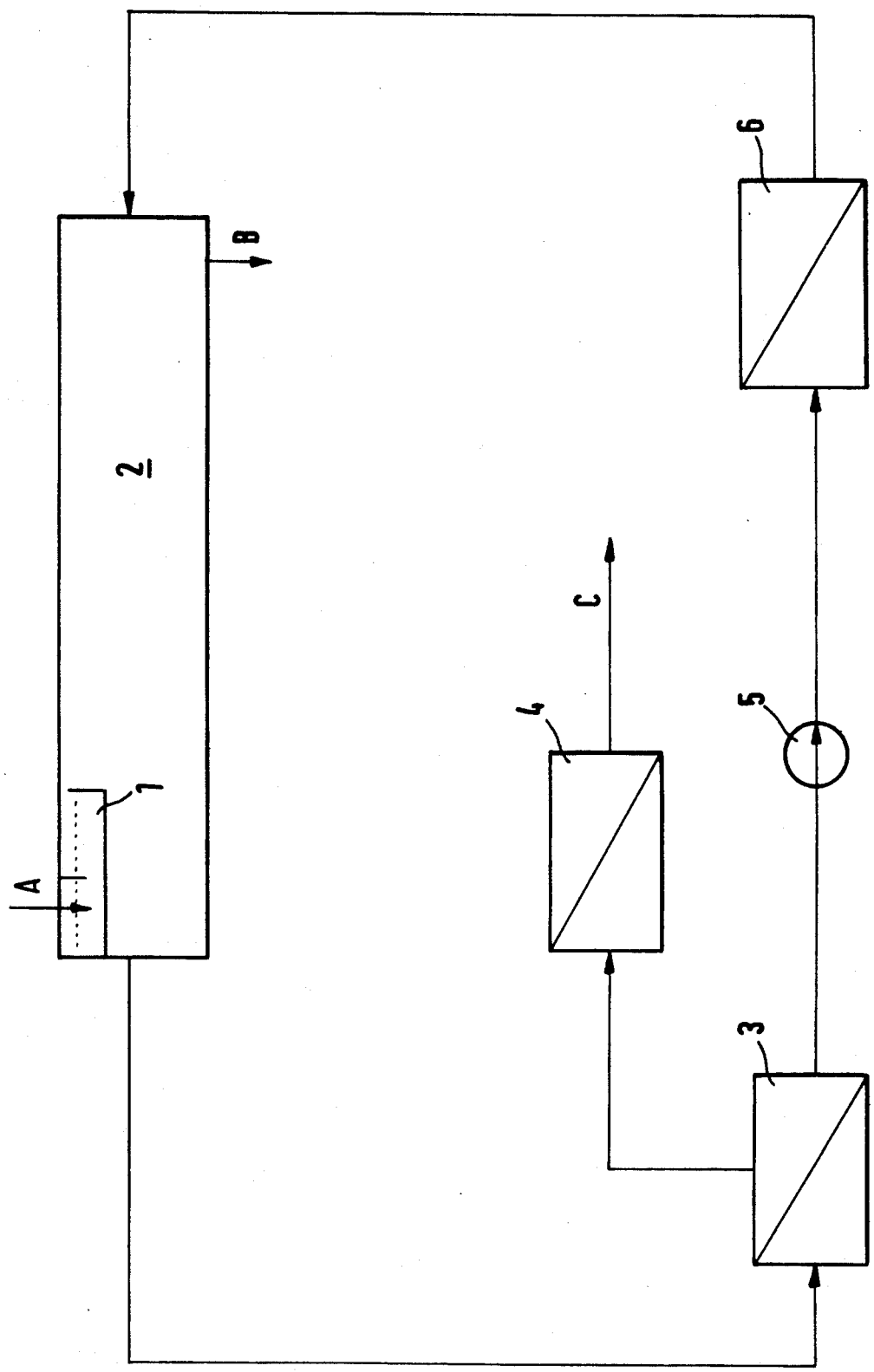

PROCESS FOR RECOVERING HALOGENATED HYDROCARBONS FROM SYNTHETIC FOAMS

BACKGROUND OF THE INVENTION

The present invention relates to a process for removing volatile, water insoluble substances from solid substances, and more particularly to a process for removing halogenated hydrocarbons from synthetic foams.

Synthetic foams, depending on their use, contain various amounts of halogenated hydrocarbons (hereinafter "FCH"). FCHs are, for example, known in Germany under the trademarks Frigen or Freon. Depending on the manufacturer, the Frigens or Freons of the type R11 and R12 are used in differing weight ratios. The major portion, however, is usually R11. A preferred application of synthetic foams is in the insulation of cooling devices, where a polyurethane foam (PUR) is used having a total content of Frigen or Freon of about 15%.

In the processing of used refrigerators, the pores of the synthetic foam are opened by comminution, compaction or a combination of both procedures for the purpose of FCH extraction. Care must be taken for reasons of environmental protection that the FCH is not released into the atmosphere, but recovered.

In a known process of the art, the FCH is released into process air which acts as a carrier medium. The FCH is then recovered by a low-temperature treatment of the process air. Due to the low vapor pressure of R11 (boiling point of 23.8° C.), however, this temperature treatment is difficult because temperatures in the order of −60° C. must be attained to achieve a good separation. The occurrence of water condensation and ice formation beforehand make the realization of this process difficult. This is even more so the case in the recovery of R12 due to an even lower boiling point of −29.8° C.

SUMMARY OF THE INVENTION

The object of the present invention is to avoid these disadvantages and to provide a process by which the recovery of FCH, particularly with respect to the temperatures employed, can be achieved without problem. According to the present invention, a process for recovering halogenated hydrocarbons is provided wherein FCH is transferred to a gaseous carrier medium of steam in a hermetically sealed processing chamber, and then separated from the steam carrier medium.

By the use of steam as the carrier medium, the following advantages result:

1) Steam as the carrier medium undergoes a phase transition in a narrow temperature range so that separation between gas and liquid is simplified;

2) FCH in the gas phase is well dissolvable in steam or water vapor, however, minimally dissolvable in the aqueous liquid phase;

3) Steam or water vapor demonstrates approximately ideal gas behavior, so that the behavior of gaseous FCH is not a problem;

4) By extracting a pure FCH gas flow, foams produced from different types of FCH can also be disposed of;

5) Despite the high vaporization enthalpy of water, the use of steam or water vapor is still energetically favorable because the good heat capacity of water vapor compared to air allows the use of a minimal carrier medium flow;

6) The use of steam avoids possible ignition of the foam material, so that an advantageous fire-safety behavior results.

Further advantageous embodiments of the process according to the present invention include the following aspects:

1) The synthetic foam is preferably treated mechanically, more particularly comminuted and/or compacted before the transfer of FCH into the steam;

2) The extraction of FCH by steam can take place under atmospheric pressure or at a slight pressure above atmosphere to avoid introduction of air into the system;

3) The separation of FCH from the carrier medium, steam, preferably takes place in a first condenser, which is formed as a cooler-separator combination. The mixture is then cooled to condense the water;

4) The gaseous FCH arising in the first condenser can then be condensed in at least one additional condensation stage, which consists of a compressor, cooler and separator, collected in liquid form and recovered; and/or 5) Water resulting from the first condenser can be fed by a pump to a steam generator and from there to the synthetic foam treatment. Therefore, water losses only occur through possible untight sealings or as small losses of steam or vapor at mechanical joints.

BRIEF DESCRIPTION OF THE DRAWINGS

The invention will be described more fully in the following conjunction with the accompanying drawing, which schematically illustrates an embodiment of the present invention as a process for the treatment of insulation foam from used refrigerators.

DESCRIPTION OF THE PREFERRED EMBODIMENTS

Synthetic foam to be treated is fed through an airtight transfer passage 1 to a treatment chamber 2 and opened up by comminution, i.e., the pores of the foam are opened. The supply of the synthetic foam is indicated by the arrow A.

The treatment chamber 2 which forms a hermetic system with respect to the surroundings is connected to a steam generator 6. The processing of the synthetic foam takes place in a steam atmosphere, i.e., at temperatures above 100° C. The released FCH is taken up in the steam. The treatment chamber 2 includes a second transfer passage (not shown) which provides for transfer lock discharge of the treated synthetic foam. The discharge of the synthetic foam is indicated by the arrow B. The discharged, treated synthetic material is a flaky material of dimensions smaller than the original pore size. The material can be compressed by a conveyance device arranged in the discharge passage and therefore substantially freed of the carrier medium, whereby very little moisture remains.

The interior of the treatment chamber 2 can have atmospheric pressure or a low gauge pressure of about 0.1 bar, to prevent the penetration of ambient air into the closed system.

The operation temperature in the treatment chamber 2 lies between the steam saturation temperature at 1 bar and the decomposition temperature of the synthetic foam.

The steam/FCH mixture extracted from the treatment chamber 2 is supplied to a first condenser 3, which is provided as a cooler-separator combination. The mixture is cooled to a temperature of 50° C. to 80° C. in the first condenser 3. The condensation water from the FCH gas flow is thus separated.

Gaseous FCH is then withdrawn from the first condenser 3 at a temperature of about 50° C. to 80° C. and condensed to liquid in a single or multi-stage condensation. This condensation is illustrated schematically by a second condenser 4, in which the FCH gas flow is completely condensed at a temperature which depends on the boiling point of the concerned FCH.

The second condenser 4 consists of a compressor, cooler and separator. The capacity of the compressor for example, on the suction side is about 100 liters of gas per cooler.

It is particularly advantageous that only the pure FCH gas flow need be treated at these temperatures, and not, however, the carrier medium flow.

The obtained FCH liquid can then be collected and reused, which is indicated by the arrow C.

Water recovered in the first condenser 3 is passed by a pump 5 to the steam generator 6 and is fed in the form of steam to the treatment chamber 2. A closed cycle is therefore established so that water losses are substantially eliminated.

The process of the invention can be particularly advantageously employed in plants for processing used refrigerators, this in an environmentally friendly manner.

The process according to the present invention has been illustrated and described in relation to recovering FCH from synthetic foams. The process, however, can also be applied whenever volatile, water insoluble substances are to be separated from solid substances.

We claim:

1. A method for recovering halogenated hydrocarbons from plastic foam, comprising subjecting plastic foam containing halogenated hydrocarbons to a steam carrier medium to transfer said halogenated hydrocarbons to said steam carrier medium, condensing said steam carrier medium and separating water from said halogenated hydrocarbons, and then compressing and condensing said halogenated hydrocarbons to liquefy said halogenated hydrocarbons.

2. A method as in claim 1, further comprising mechanically treating said plastic foam prior to subjecting said plastic foam to said steam carrier medium.

3. A method as in claim 2, wherein said mechanical treatment comprises compacting and/or comminuting said plastic foam.

4. A method as in claim 2, wherein said mechanical treatment is conducted in a hermetically-sealed environment.

5. A method as in claim 1, wherein said plastic foam is subjected to said steam carrier medium at atmospheric pressure in a hermetically-sealed environment.

6. A method as in claim 1, wherein said plastic foam is subjected to said steam carrier medium at a pressure higher than atmospheric pressure in a hermetically-sealed environment to prevent ambient air from entering said environment.

7. A method as in claim 1, further comprising compressing said plastic foam to separate said plastic foam from said steam carrier medium after subjecting said plastic foam to said steam carrier medium.

* * * * *